| United States Patent [19] | [11] Patent Number: 4,835,337 |
| Shimizu et al. | [45] Date of Patent: May 30, 1989 |

[54] METHOD FOR PRODUCING M-ETHYLDIPHENYLS

[75] Inventors: Isoo Shimizu; Yasuo Matsumura; Kazumichi Uchida, all of Yokohama, Japan

[73] Assignee: Nippon Petrochemicals Company, Limited, Japan

[21] Appl. No.: 165,730

[22] Filed: Mar. 9, 1988

[30] Foreign Application Priority Data

Mar. 10, 1987 [JP] Japan .................................. 62-54859

[51] Int. Cl.$^4$ ................................................ C07C 5/22
[52] U.S. Cl. ..................... 585/471; 585/472; 585/473; 585/474; 585/475; 585/477; 585/481
[58] Field of Search ............... 585/471, 472, 473, 473, 585/475, 477, 481

[56] References Cited

U.S. PATENT DOCUMENTS

| 4,493,943 | 1/1985 | Sato et al. | 585/25 |
| 4,642,730 | 2/1987 | Sato et al. | 585/471 |
| 4,731,483 | 3/1988 | Shimuzu et al. | 585/459 |
| 4,734,528 | 3/1988 | Shimuzu et al. | 585/459 |

*Primary Examiner*—Curtis R. Davis
*Attorney, Agent, or Firm*—Scully, Scott, Murphy & Presser

[57] ABSTRACT

A method for producing efficiently a highly pure 1-(m-ethylphenyl)-1-phenylethane or m-ethylphenyl-phenylmethane which are used as the starting materials for preparing medicines and other organic compounds. The method comprises the step of reacting a diaryl compound with benzene or alkylbenzene in the presence of an acid catalyst selected from the group consisting of AlCl$_3$, AlBr$_3$, HF.BF$_3$ complex and Y-type zeolites.

4 Claims, No Drawings

METHOD FOR PRODUCING M-ETHYLDIPHENYLS

BACKGROUND OF THE INVENTION (1) Field of the Invention

This invention relates to a method for efficiently producing high-purity 1-(m-ethylphenyl)-1-phenylethane or m-ethylphenylphenylmethane (hereinafter referred to as m-ethyldiphenyls). More particularly, it relates to a method for producing the m-ethyldiphenyls efficiently in a high state of purity which are useful as the raw materials in fields of medicine and organic synthesis.

(2) Description of the Prior Art

α-Arylpropionic acids which are profen series anodynes have highly antiphlogistic, anti-inflammatory, analgesic and febrifugal effects, and therefore, they are used as drugs. Of these profen series anodynes, α-(m-benzoylphenyl)propionic acid which is usually called Ketoprofen (trade name) is the good anodyne having high efficacy. For this reason, various producing methods have been suggested in which it is attempted to prepare Ketoprofen inexpensively in a high purity. Of these suggested methods, a method of using the m-ethyldiphenyls as raw materials is considered to be preferable in that a synthetic route is short.

Thus, the method for producing the m-ethyldiphenyls in a high purity which are considered to be preferable as raw materials for the synthesis is demanded, but conventional methods are not always satisfactory, since they cannot synthesize the meta-substituted compound selectively with ease. For example, as methods for synthesizing m-ethylphenylphenylmethane, there are a method of using m-ethylphenol as a starting material in accordance with the Grignard reaction [J. Amer. Chem. Soc., Vol. 76, 5108 (1954)]and other methods, merely preparing a mixture of the aimed product [J. Amer. Chem. Soc., Vol. 84, 1688 (1962) and J. Amer. Chem. Soc., Vol. 91, 7192 (1969)].

Furthermore, as a method for producing 1-(m-ethylphenyl)-1-phenylethane, there is a method of obtaining ethyldiphenylethane in the form of a mixture by alkylating diphenylethane with ethylene.

In the above methods which have already been disclosed, the synthesis involves combining complicated multistage reactions and using expensive starting materials, or alternatively the mixture containing ortho-, meta- and para-substituted compounds can be only obtained. That is, the conventional methods require complicated steps toward the intended end product or are inevitably accompanied by the by-product of at least the ortho-substituted compound.

Here, boiling points of the respective ethyl group position isomers of the ethyldiphenyls are shown in the following Tables 1 and 2.

TABLE 1

| Physical Properties of 1-(Ethylphenyl)-1-phenylethanes | |
| --- | --- |
| Substituted Compound | Boiling Point (°C.) |
| Ortho-substituted Compound | 285 |
| Meta-substituted Compound | 284 |
| Para-substituted Compound | 293 |

TABLE 2

| Physical Properties of Ethylphenylphenylmethanes | | |
| --- | --- | --- |
| Substituted Compound | b.p. (°C.) | m.p. (°C.) |
| Ortho-substituted Compound | 290.9 | −11.2 |
| Meta-substituted Compound | 291.5 | −9.2 |
| Para-substituted Compound | 297.0 | −23.5 |

(all the b.p.'s are in terms of atmospheric pressure)

As exhibited in the above tables, the ortho- and meta-substituted compounds are substantially similar to each other in physical properties such as the boiling points and melting points, and therefore, any of them cannot be separated from others by a conventional separating means, for example, distillation. If an elaborate separating process is used, the obtained product will be rather expensive and unecomonical. Therefore, it can be concluded that the method in which ortho-substituted compounds are formed as by-products cannot provide the pure meta-substituted compound economically and inexpensively

SUMMARY OF THE INVENTION

The inventors of the present application have found that only meta- and para-substituted compounds are produced as ethyldiphenyls by a certain treatment under particular conditions, and this invention has been accomplished on the basis of this finding.

In this invention, the meta- and para-substituted compounds alone are produced as the ethyldiphenyls, and the ortho-substituted compound is not substantially formed as a by-product. In consequence, the desired meta-substituted compound can be easily separated from the para-substituted compound by a conventional separating means such a distillation, with the result that the high-purity metasubstituted compound (m-ethyldiphenyls) can be obtained.

That is, according to this invention, there is provide a method for producing 1-(m-ethylphenyl)-1-phenylethane or m-ethylphenylphenylmethane which comprises the step of bringing diphenylmethane, 1,1-diphenylethane, a monoethyl-substituted compound in which these compounds are substituted at a position other than the meta-position with an ethyl group, polyethyldiphenylmethane, polyethyl-1,1-diphenylethane or a mixture thereof into contact with benzene, an ethyl-substituted benzene in which at least one ethyl group is substituted, or a mixture thereof in the presence of an acid catalyst selected from the group consisting of AlCl3, AlBr3, HF.BF3 complex and Y type zeolites. This method can provide the above compounds in high purity which are preferable as raw materials for synthesis of medicines and the like.

DETAILED DESCRIPTION OF THE INVENTION

In this invention, there is used benzene or an ethyl-substituted benzene which is substituted by at least one ethyl group (hereinafter referred to generically as "alkylbenenes"). Typical examples of the ethyl-substituted benzenes which can be used in this invention include ethylbenzene, diethylbenzene, triethylbenzene and tetraethylbenzene. Even when an ethyl group-substituted benzene has two or more ethyl groups, it can be used in this invention, since substituted positions of the ethyl groups are not critical. Furthermore, the alkylbenzenes may be used singly or in the form of a mixture thereof. Each of these alkylbenzenes can be easily obtained by alkylating benzene with, for example, ethylene, ethylene chloride or ethyl alcohol.

Furthermore, as the other raw material which is used in the reaction in this invention, there is diphenylmethane, 1,1-diphenylethane, a monoethyl group-substituted compound in which any of the above compound is substituted at a position except for the meta-position by one ethyl group, polyethyldiphenylmethane, or polyethyl-1,1-diphenylethane (hereinafter referred to generically as "diaryls"). Examples of these diaryls are as follows: First, examples of diarylmethanes include diphenylmethane, ethyldiphenylmethane, diethyldiphenylmethane, triethyldiphenylmethane and tetraethyldiphenylmethane; and examples of diarylethanes include 1,1-diphenylethane, ethyl-1,1-diphenylethane, diethyl-1,1-diphenylethane, triethyl-1,1-diphenylethane, tetraethyl-1,1-diphenylethane, pentaethyl-1,1-diphenylethane, heptaethyl-1,1-diphenylethane and octaethyl-1,1diphenylethane. The number of ethyl groups as substituents in each of these diaryls is not limited, and positions of the substitutent ethyl groups may be symmetrical or asymmetrical. However, monoethyldiphenylmethane or monoethyl-1,1-diphenylethane which is a monoethyl group-substituted compound is a compound in which the ethyl group is bound on a position other than the meta-position. More particular examples of these monoethyl group-substituted compounds include 1-(p-ethylphenyl)-1-phenylethane, 1-(o-ethylphenyl)-1-phenylethane, p-ethylphenylphenylmethane and o-ethylphenylphenylmethane. These diaryls may be used singly or in the form of a mixture thereof. Needless to say, the compound which is substituted at the m-position by a monoethyl group can be included in the raw material of this invention.

These diaryls can be easily prepared by a conventional known process. For example, the diarylmethane can be prepared in accordance with a method of reacting polyethylbenzene, occasionally having an ethyl group, with formaldehyde or paraformaldehyde by the use of a sulfuric acid catalyst; a method of reacting polyethylbenzene with methylene chloride by the use of an aluminum chloride catalyst; and a method of reacting polyethylbenzene with benzyl chloride in the presence of a Friedel-Crafts catalyst. Furthermore, as methods for preparing the diarylethanes, there are a method of reacting polyethylbenzene with acetaldehyde or paraldehyde in the presence of a sulfuric acid catalyst; a method of reacting polyethylbenzene with 1,1-dichloroethane by the use of an aluminum chloride catalyst; a method of reacting polyethylbenzene with styrene in the presence of an acid catalyst; and a method of reacting polyethylbenzene with α-chloroethylbenzene.

Here, according to another way of the elucidation, the diaryls and the alkylbenzenes used as raw materials in this invention can be represented by the following formulae (I) and (II) respectively:

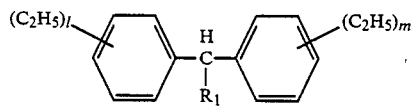

(I)

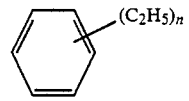

(II)

wherein $R_1$ is a hydrogen atom or a methyl group, and each of l, m and n is 0 or an integer of 1 or more, and the total of these integers is 1 or more. Moreover, when $l+m=1$ in the formula (I), the substituent ethyl group is bound on a position other than the m-position.

The catalyst used in this invention is an acid catalyst selected from the group consisting of $AlCl_3$, $AlBr_3$, $HF \cdot BF_3$ complex and Y-type zeolites. These catalysts may be used singly or in the form of a mixture thereof. The amount of the catalyst is usually 0.01% by weight or more based on the weight of the reaction materials. The upper limit of the amount is not particularly limited and can be chosen suitably, but a practical level of the upper limit can be considered to be about 50% by weight from the viewpoints of costs for catalyst separation and neutralization.

In this invention, the alkylbenzenes and the diaryls are brought into contact with the above-mentioned acid catalyst in a liquid phase under the conditions that they can be sufficiently homogeneously mixed. In order to achieve the mixing conditions, a batch system reactor equipped with a stirrer or a continuous system reactor such as a packed column having a high contact efficiency may be employed. A temperature which is one of the aforesaid contact conditions is from −10° to 200° C., and preferably from 0° to 180° C. When the contact temperature is below −10° C., the production of the meta-substituted compound is undesirably poor. Inversely, when the temperature is above 200° C., the loss of ethyl group contained in the raw materials increases and the amount of a heavy tarry substance increases significantly, which is unpreferable. Pressure which is the other factor of the contact conditions is suitably selected so that the contact can be conducted in the state of a liquid phase at the above contact temperature. In the case of the batch system, an enough contact time is usually within 8 hours. A longer contact time than 8 hours is rather unpreferable, since it causes the increase of the formation of heavy tarry substance.

In the method of this invention, m-ethyldiaryls such as 1-(m-ethylphenyl)-1-phenylethane and m-ethylphenylphenylmethane are produced. Therefore, it is necessary that one or both of the alkylbenzenes and the diaryls which are the starting materials have at least one ethyl group.

In the contact of this invention, therefore, the ratio of the total of the mole number of benzene rings in the alkylbenzenes which are the raw materials and the mole number of diphenyl ring structures in the diaryls which are the other raw materials to the total of the mole number of the ethyl groups in the alkylbenzenes and the mole number of the ethyl groups in the diaryls is preferably from 0.05 to 20, and more preferably from 0.1 to 10. When the mole number of the ethyl groups in the raw material mixture is originally small, the ratio of the mole numbers is in excess of 20, and therefore the concentration of the ethyl groups in the reaction mixture of the m-ethyldiphenyls which are the end products is low, which is not economical in view of recovery efficiency. Inversely, when the ratio of the molar numbers is below 0.05, the loss of the ethyl group increases and the amount of the heavy tarry substance increases significantly, which is not preferable. In addition, a ratio of the mole number of the alkylbenzenes which are the first raw materials to the mole number of the diaryls which are the second raw materials is preferably 40 or below, more preferably 20 or below. When the ratio exceeds this level, the recovery efficiency of the desired product is unpreferably low.

When the contact of this invention is carried out under the above-mentioned conditions, there occur an apparent disproportionation that the ethyl groups of the akylbenzenes are transferred to the diaryls, and the isomerization due to the transfer of the ethyl groups in the diaryls. As a result of the apparent disproportionation and the isomerization, a fraction of the monoethyldiphenyls consisting of meta- and para-substituted compounds alone is formed in the reaction mixture after the contact. According to this invention, the produced fraction of the monoethyldiphenyls is composed of only meta- and para-substituted compounds and is substantially free from the ortho-substituted compound. For example, even if 1-(o-ethylphenyl)-1-phenylethane or o-ethylphenylphenylmethane is used as a raw material, this compound is not substantially found in the prepared reaction mixture. As described above, the meta and para-substituted compounds are considerably different from each other in physical properties. For this reason, the meta-substituted compound can be separated from the para-substituted compound by the conventional physical means. Therefore, when the reaction mixture is separated by an industrially prevalent separating means, for example, a distillation means, high-purity 1-(m-ethylphenyl)-1-phenylethane or m-ethylphenylphenylmethane can be produced with ease. Conditions for the distillation, for example, the degree of reduced pressure, the ratio of refluxing and the like can be suitably decided, taking purity of the product, economical effeciency and the like into consideration.

The remaining fraction of the reaction mixture from which the desired m-ethyldiphenyls ave been separated by the method of this invention can be brought into contact with the acid catalyst as the raw material in the next process of this invention in order to be converted into the desired m-ethyldiphenyls, though the acceptance of such a treatment depends on a composition of the remaining fraction. That is, a fraction which can be separated and recovered as a fraction lighter than the desired m-ethyldiphenyls is benzene, ethylbenzene, an alkylbenzene such as diethylbenzene, 1,1-diphenylethane, or diphenylmethane. Further, a fraction which can be separated and recovered as a fraction heavier than the desired product is 1-(p-ethyl- phenyl)-1-phenylethane, p-ethylphenylphenylmethane, polyethyl-1,1-diphenylethane or polyethyldiphenylmethane having two or more ethyl groups. These lighter and heavier fractions which have been separated and recovered can be refined in compliance with a purpose, or can be treated again as the raw materials in accordance with the method of the present invention.

As described above, according to this invention, m-ethyldiaryls such as 1-(m-ethylphenyl)-1-phenylethane and m-ethylphenylphenylmethane can be obtained inexpensively and easily in a high purity. In the reaction mixture of this invention, 1-(o-ethylphenyl)-1-phenylethane or o-ethylphenylphenylmethane are not contained substantially, and therefore, high-purity 1-(m-ethylepheny)-1-phenylethane or m-ethylphenylmethane can easily be produced by the usual separating means such as distillation.

Now, this invention will be described by way of examples.

EXAMPLE 1

In a 3-liter reactor were placed 1,060 g of ethylbenzene and 336 g of diphenylmethane, and the temperature in the reactor was maintained at 25° to 35° C. While the mixture was stirred, 45 g of anhydrous $AlCl_3$ was added thereto, and the stirring was further continued for 4 hours to perform reaction. After the reaction, 300 ml of 5% hydrochloric acid was added thereto to inactivate the catalyst. Washing was then repeated with water until a water layer had been neutralized, and the resulting reaction liquid was analyzed by gas chromatography and the resulting product was separated by distillation. The results of the gas chromatography are set forth in Table 3.

The reaction product was distilled under reduced pressure to obtain 77 g of a fraction mainly comprising ethyldiphenylmethane at a distillation temperature of 120° to 145° C. at 2 to 3 mmHg. In this fraction, a trace of o-ethyldiphenylmethane was contained, and the fraction was substantially composed of m- and p-ethyldiphenylmethane alone and the ratio of the m-isomer to the p-isomer was 2.7.

Afterward, the thus prepared fraction was rectified to obtain 53 g of a fraction containing 98% of m-ethyldiphenylmethane at a distillation temperature of 127 to 130° C. at 2 to 3 mmHg.

EXAMPLE 2

In the same manner as in Example 1, 1,060 g of ethylbenzene and 364 g of 1,1-diphenylethane were placed in a 3-liter reactor, and the temperature in the reactor was maintained at 25° to 35° C., and 20 g of anhydrous $AlBr_3$ was added thereto with stirring, and the stirring was further continued out for 4 hours to perform reaction. After the reaction, 300 ml of 5% hydrochloric acid was added thereto to inactivate the catalyst. Washing was then repeated with water until a water layer had been neutralized, and the resulting reaction liquid was analyzed by gas chromatography and the resulting product was separated by distillation. The results of the gas chromatography are set forth in Table 3.

The reaction product was then distilled under reduced pressure to obtain 91 g of a fraction mainly comprising 1-(ethylphenyl)-1-phenylethane at a distillation temperature of 120° to 145° C. at 2 to 3 mmHg. In this fraction, 1-(o-ethylphenyl)-1-phenylethane was not contained, and the fraction was composed of m- and p-isomers of 1-(ethylphenyl)-1-phenylethane alone and the ratio of the m-isomer to the p-isomer was 2.2.

Afterward, the thus prepared fraction was rectified to obtain 58 g of a fraction containing 97% of 1-(m-ethylphenyl)-1-phenylethane at a distillation temperature of 125° to 129° C. at 2 to 3 mmHg.

EXAMPLE 3

In a 200-milliliter anticorrosive autoclave equipped with a stirrer were placed 53 g of ethylbenzene and 17 g of diphenylmethane, and after cooling with ice, 3 g of $HF\cdot BF_3$ was added thereto. The temperature in the vessel was maintained at 25° to 35° C., and the mixture was then stirred for 6 hours to perform reaction. After the reaction, the reaction product was cooled with ice again and wa poured gradually into ice water in order to inactivate the catalyst. Washing was then repeated with water until a water layer had been neutralized, and the resulting reaction liquid was analyzed by gas chromatography.

According to the results of the analysis, a fraction corresponding to ethyldiphenylmethanes was present in a ratio of 6.3% and contained 4.7% of m-ethyldiphenylmethane and 1.6% of p-ethyldiphenylmethane. Only a trace of o-ethyldiphenylmethane was confirmed.

EXAMPLE 4

In a 1-liter reactor were placed 500 g of mixed diethylbenzene and 100 g of concentrated sulfuric acid, and a mixture of 170 g of a diethylbenzene mixture and 104 g of styrene was then added dropwise thereto over about 1.5 hours under ice cooling. Stirring was further carried out for 1 hour to perform reaction. After the reaction, the reaction liquid was then allowed to stand, and the separation of an organic layer, neutralization and distillation under reduced pressure were carried out in turn to obtain 175 g of a diethyldiphenylethane fraction mainly comprising 1-(diethyl- phenyl)-1-phenylethane at a distillation temperature of 135° to 165° C. at 2 to 3 mmHg.

In a 200-milliliter reactor were placed 47 g of benzene, 54 g of diethylbenzene and 48 g of the diethyldiphenylethane fraction prepared by the above reaction, and the temperature in the reactor was maintained at 25° to 35° C., and 2 g of anhydrous AlCl$_3$ was added thereto with stirring, and the stirring was further continued for 4 hours to perform reaction. After the reaction, 20 ml of 5% hydrochloric acid was added thereto so as to inactivate the catalyst. Washing was then repeated with water until a water layer had been neutralized, and the resulting reaction liquid was analyzed by gas chromatography.

According to the results of the analysis, a fraction corresponding to ethyldiphenylethanes was present in a ratio of 7.3% and contained 5.3% of 1-(m-ethylphenyl)-1-phenylethane and 2.1% of 1-(p-ethylphenyl)-1-phenylethane. In the fraction corresponding to the ethyldiphenylethanes, any presence of 1-(o-ethyldiphenyl)-1-phenylethane was not confirmed.

EXAMPLE 5

In a 3-liter reactor were placed 1,000 g of benzene and 20 g of anhydrous AlCl$_3$, and the temperature in the reactor was maintained at 5° to 10° C. under ice cooling, and 100 liters of an ethylene gas was gradually introduced into the reactor. After the reaction, 300 ml of 5% hydrochloric acid was added thereto so as to inactivate the catalyst. Washing was then repeated with water until a water layer had been neutralized, and the resulting reaction liquid was distilled under reduced pressure to obtain 390 g of a mixed fraction containing polyethylbenzene having 1 to 3 ethyl groups at a distillation temperature of 55° to 120° C. at 20 to 25 mmHg.

In a 1-liter reactor were placed 200 g of the above mixed fraction and 100 g of concentrated sulfuric acid, and after ice cooling, a mixture of 100 g of the above mixed fraction and 40 g of acetaldehyde was added dropwise thereto gradually with vigorous stirring. After reaction, the resulting sulfuric layer was separated, followed by neutralizing and water washing. Distillation was then carried out under reduced pressure to obtain 110 g of a 1,1-bis(polyethylphenyl)ethane fraction at a distillation temperature of 145° to 210° C. at 2 to 3 mmHg.

In a 200-milliliter reactor were placed 110 g of benzene and 42 g of the above obtained 1,1-bis(polyethylphenyl)ethane fraction, and the temperature in the reactor was maintained at 25° to 35° C. Afterward, 2 g of anhydrous AlCl$_3$ was added thereto with stirring, and the stirring was further continued for 4 hours to perform reaction. After the reaction, 20 ml of 5% hydrochloric acid was added thereto so as to inactivate the catalyst. Washing was then repeated with water until a water layer had been neutralized, and the resulting reaction liquid was analyzed by gas chromatography.

According to the results of the analysis, a fraction corresponding to ethyldiphenylethanes was present in a ratio of 8.6% and contained 6.1% of 1-(m-ethylphenyl)-1-phenylethane and 2.5% of 1-(p-ethylphenyl)-1-phenylethane. In this fraction corresponding to the ethyldiphenylethanes, any presence of 1-(o-ethyldiphenyl)-1-phenylethane was not confirmed.

EXAMPLE 6

In Example 1, the reaction product had been distilled under reduced pressure to obtain a fraction mainly comprising ethyldiphenylmethanes at a distillation temperature 120° to 145° C. at 2 to 3 mmHg, and the leftover fractions had been then obtained into a lighter fraction and heavier fractions than the ethyldiphenylmethane fraction. In this Example 6, reaction was performed by the use of these lighter and heavier fractions. The lighter fraction contained ethylbenzene and polyethylbenzenes as main components and the heavier fraction contained polyethyldiphenyl methanes as main components.

The lighter fraction and the heavier fraction prepared by the distillation in Example 1 were distilled again to obtain 860 g of a fraction of from a distillation temperature of 80° C. at atmospheric pressure to a distillation temperature of 165° C. at 2 to 3 mmHg.

To 105 g of the fraction obtained by the above redistillation were added 33 g of diphenylmethane and 3 g of AlCl$_3$, and reaction was performed in the like manner as in Example 1.

After the reaction, gas chromatography analysis followed. According to the results, in a 5.8% fraction corresponding to ethyldiphenylmethanes, only a trace of o-ethyldiphenylmethane was contained, and the fraction was substantially composed of m- and p-ethyldiphenylmethane alone and an existent ratio of the m-isomer to the p-isomer was 2.4.

EXAMPLE 7

In a 200-milliliter reactor were placed 135 g of benzene and 55 g of the 1,1-bis(polyethylphenyl)ethane fraction prepared in Example 5, and the temperature in the reactor was maintained at 135° to 140° C. While the mixture was stirred, 8.2 g of an H-Y type zeolite (Catalyst & Chemicals Industries Co., Ltd.) was added thereto, and the stirring was further continued for 4 hours to perform reaction. After the reaction, the catalyst was separated out by filtration, and the reaction liquid was analyzed by gas chromatography.

According to the analytical results, a fraction corresponding to ethyldiphenylethanes was present in a ratio of 11.3%, and a component ratio of 1-(m-ethylphenyl)-1-phenylethane to 1-(p-ethylphenyl)-1-phenylethane was 2.9. In this fraction, any presence of 1-(o-ethylphenyl)-1-phenylethane was not confirmed.

EXAMPLE 8

The combined fraction of the lighter and heavier fractions used in Example 6 was redistilled to obtain 200 g of a distillate in the temperature range of 80° C. at atmospheric pressure to 165° C. at 2 to 3 mmHg. To this distillate were added 53 g of diphenylmethane and 14 g of H-Y type zeolite (by Catalyst & Chemicals Industries Co., Ltd.). Afterward, reaction was performed in the like manner as in Example 7.

After the reaction, gas chromatographic analysis was carried out. According to the results, in a 7.6% fraction corresponding to ethyldiphenylmethanes, any presence of o-ethyldiphenylmethane was not detected, and the ratio of the m-isomer to the p-isomer was 2.6.

TABLE 3

| Analytical Results by Gas Chromatography | | |
| --- | --- | --- |
| Compound | Example 1 (%) | Example 2 (%) |
| Benzene | 22.2 | 21.2 |
| Ethylbenzene | 51.4 | 45.1 |
| Diethylbenzenes | 11.5 | 17.3 |
| Triethylbenzenes | 0.5 | 0.9 |
| Raw Material Diphenyls | 4.4 | 4.6 |
| Ethyldiphenylmethane or Ethyldiphenylethane | 6.4 | — |
|  | — | 7.4 |

TABLE 3-continued

| Analytical Results by Gas Chromatography | | |
| --- | --- | --- |
| Compound | Example 1 (%) | Example 2 (%) |
| Diethyldiphenyls | 3.6 | 3.6 |

What is claimed is:

1. A method for producing 1-(m-ethylphenyl)-lphenylethane which comprises contacting 1,1-diphenylethane, a monoethyl 1,1-diphenylethane wherein said monoethyl 1,1-diphenylethane is not the meta-isomer, a polyethyl 1,1-diphenylethane or a mixture thereof, with benzene, ethyl benzene, a polyethyl benzene, or a mixture thereof, in the presence of an acid catalyst, wherein said acid catalyst is $AlCl_3$, $AlBr_3$, $HF \cdot BF_3$ complex or a y-type zeolite.

2. A method for producing m-ethylphenylphenylmethane which comprises contacting diphenylmethane, a monoethyl diphenylmethane wherein said monoethyl diphenylmethane is not the meta-isomer, a polyethyldiphenylmethane, or a mixture thereof, with benzene, ethyl benzene, a polyethyl benzene, or a mixture thereof, in the presence of an acid catalyst, wherein said acid catalyst is $AlCl_3$, $AlBr_3$, $HF \cdot BF_3$ complex or a y-type zeolite.

3. The method according to claim 1 or 2 wherein after the contact with said acid catalyst, separation is carried out by distillation.

4. The method according to claim 1, wherein said contact is carried out in the liquid phase at the temperature range of -10° to 200° C.

* * * * *

UNITED STATES PATENT AND TRADEMARK OFFICE
CERTIFICATE OF CORRECTION

PATENT NO. : 4,835,337
DATED     : May 30, 1989
INVENTOR(S) : Isoo Shimizu, et al.

It is certified that error appears in the above-identified patent and that said Letters Patent is hereby corrected as shown below:

Column 10, lines 9-10, Claim 1: "-1phenylethane" should read as -- -1-phenylethane--

Column 10, line 30, Claim 4: "according to claim 1" should read as --according to claim 1 or 2--

Signed and Sealed this

Thirteenth Day of February, 1990

Attest:

JEFFREY M. SAMUELS

Attesting Officer

Acting Commissioner of Patents and Trademarks